(12) United States Patent
Pei et al.

(10) Patent No.: US 9,498,451 B2
(45) Date of Patent: Nov. 22, 2016

(54) METHOD FOR TREATING OR PREVENTING RADIATION DAMAGE

(71) Applicant: Beijing Institute of Transfusion Medicine, Academy of Military Medical Sciences, Beijing (CN)

(72) Inventors: Xuetao Pei, Beijing (CN); Yanhua Li, Beijing (CN); Sihan Wang, Beijing (CN); Jing Zhang, Beijing (CN); Hailei Yao, Beijing (CN); Wei Shi, Beijing (CN); Wen Yue, Beijing (CN)

(73) Assignee: BEIJING INSTITUTE OF TRANSFUSION MEDICINE, ACADEMY OF MILITARY SCIENCES, Beijing (CN)

( * ) Notice: Subject to any disclaimer, the term of this patent is extended or adjusted under 35 U.S.C. 154(b) by 0 days.

(21) Appl. No.: 14/763,384

(22) PCT Filed: Jan. 23, 2014

(86) PCT No.: PCT/CN2014/071281
§ 371 (c)(1),
(2) Date: Jul. 24, 2015

(87) PCT Pub. No.: WO2014/114254
PCT Pub. Date: Jul. 31, 2014

(65) Prior Publication Data
US 2015/0359758 A1 Dec. 17, 2015

(30) Foreign Application Priority Data

Jan. 25, 2013 (CN) .......................... 2013 1 0030532

(51) Int. Cl.
*A61K 31/13* (2006.01)
*A61K 31/132* (2006.01)

(52) U.S. Cl.
CPC ............. *A61K 31/132* (2013.01); *A61K 31/13* (2013.01)

(58) Field of Classification Search
None
See application file for complete search history.

(56) References Cited

FOREIGN PATENT DOCUMENTS

| CN | 101716167 A | 6/2010 |
|---|---|---|
| CN | 102389408 A | 3/2012 |
| CN | 102573822 A | 7/2012 |
| CN | 103110613 A | 5/2013 |

OTHER PUBLICATIONS

CAPLUS 1990:25661.*
International Search Report dated Apr. 16, 2014 for related PCT application No. PCT/CN2014/071281, filed Jan. 23, 2014.

* cited by examiner

*Primary Examiner* — Heidi Reese
(74) *Attorney, Agent, or Firm* — Z. Peter Sawicki; Westman, Champlin & Koehler, P.A.

(57) ABSTRACT

Disclosed in the present invention is new use of saturated amine compounds for use in preparing medicines to resist radiation damage and promoting regeneration and repair of radiation-damaged tissues.

9 Claims, 3 Drawing Sheets

METHOD FOR TREATING OR PREVENTING RADIATION DAMAGE

CROSS-REFERENCE TO RELATED APPLICATION

The present application is the U.S. national phase of PCT Application No. PCT/CN2014/071281 filed on Jan. 23, 2014, which claims a priority to Chinese Patent Application. No. 201310030532.5 filed on Jan. 25, 2013, the disclosures of which are incorporated in their entirety by reference herein.

FIELD

The present disclosure relates to a new use of a compound, in specific to a use of a saturated amines compound in preparation of a medicament for resisting a radiation damage or improving regeneration and repair of a radiation-damaged tissue.

BACKGROUND

With the development of society, the development of an atomic energy has brought lots of convenience for national defense and human lives. However, nuclear radiation brings a significant danger and potential security risk to the current world, which seriously challenges the health and security of human bodies. The reason is radiation may seriously harm the health of a human body, which directly acts on DNA, proteins, and enzymes, causes ionization to excite chemical bonds to break, and therefore denatures the molecule and destroys the cell structure. The radiation further acts on water molecules in an organism, causes the water molecule to ionize and excite to generate large amounts of strong oxidative free radicals, and indirectly denatures, destroys and kills the cell, such that the organism may have a series of diseases such as metabolic disorder, intestine dysfunction, hemopoietic tissue dysfunction, nervous system dysfunction, immune system dysfunction, and endocrine system dysfunction. In addition, although being important curing means for some malignant and benign diseases right now, the application of radiation therapy is still limited due to its damages to normal tissues. Therefore, it is of great significance to improve treatments and researches of damages caused by nuclear radiations.

However, researches on the medicaments for resisting a radiation damage and improving regeneration and repair of a radiation-damaged tissue still need to be improved.

SUMMARY

The present disclosure seeks to solve at least one of the problems existing in the prior art. To this end, an object of the present disclosure is to provide a compound for preparing a medicament for resisting a radiation damage and improving regeneration and repair of a radiation-damaged tissue. Specifically, the present disclosure provides in embodiments a new use of a saturated amines compound, i.e. use in preparation of a medicament for resisting a radiation damage and improving regeneration and repair of a radiation-damaged tissue.

It should be noted that, the present disclosure is achieved based on the following discoveries by the inventor.

At present, it has been achieving a certain development in exploring radioresistance with synthetic compounds, nature medicines and biological factors, as well as corresponding basic arrangements and researches thereof. Existing radiation resistant agents, also referred to as medicaments for resisting a damage caused by radiation, mainly include sugars, phenols, hormones, vitamins, a nucleic acid precursor, conventional medicated diets, organic acids, esters, peptides, etc. However, recent researches on a radio-protective agent still need to be improved.

During researches, the inventors of the present disclosure find out that a saturated amines compound (with a code of TA01) is capable of improving a recovery of a radiation-damaged hematopoietic system; increasing contents of white blood cell (WBC), red blood cell (RBC), platelet (PLT) in peripheral blood of a radiation-damaged mouse, respectively; increasing the number of all nucleated cells and the number of hematopoietic stem/progenitor cells in bone marrow (i.e., the number of CFU; the number of CFU-G, CFU-GM and CFU-MK), and well-repairing intestinal, hepatic and pulmonary tissues of the irradiation-damaged mouse, thereby increasing a survival rate of radiation-damaged mice significantly.

Therefore, in one aspect, the present disclosure provides in embodiments a use of a saturated amines compound in preparation of a medicament for resisting a radiation damage and improving regeneration and repair of a radiation-damaged tissue. Thereby, based on the new use of the above-identified saturated amines compound, the saturated amines compound (TA01) may be used to prepare a medicament for resisting a radiation damage. Further, damaged cells and tissues may be effectively repaired by administrating the medicament for resisting a radiation damage to a human or animal suffering a radiation damage. Specifically, the saturated amines compound may improve a recovery of a radiation-damaged hematopoietic system; in other words, the saturated amines compound may increase contents of WBC, RBC and PLT in peripheral blood, respectively; increase the number of all nucleated cells and the number of hematopoietic stem/progenitor cells in bone marrow (the number of CFU; and the number of CFU-G, CFU-GM and CFU-MK), and repair intestinal, hepatic and pulmonary tissues.

In addition, the new use of the saturated amines compound according to the above embodiments of the present disclosure may have the following additional technical features.

According to some embodiments of the present disclosure, the saturated amines compound is represented by the following formula I:

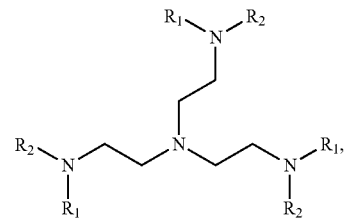

wherein each $R_1$ is independently H, $CH_3$ or $CH_2CH_3$; and each $R_2$ is independently H, $CH_3$ or $CH_2CH_3$.

Specifically, according to an embodiment of the present disclosure, $R_1$ is $CH_3$, $R_2$ is $CH_3$, and the saturated amines compound is tris(2-(dimethylamino)ethyl)amine.

According to another embodiment of the present disclosure, $R_1$ is H, $R_2$ is H, and the saturated amines compound is N1,N1-bis(2-aminoethyl)ethane-1,2-diamine.

According to yet another embodiment of the present disclosure, $R_1$ is H, $R_2$ is $CH_3$, and the saturated amines compound is N1-methyl-N2,N2-bis(2-(methylamino)ethyl)ethane-1,2-diamine.

According to still yet another embodiment of the present disclosure, $R_1$ is H, $R_2$ is $CH_2CH_3$, and the saturated amines compound is N1-ethyl-N2,N2-bis(2-(ethylamino)ethyl)ethane-1,2-diamine.

According to yet another embodiment of the present disclosure, $R_1$ is $CH_2CH_3$, $R_2$ is $CH_2CH_3$, and the saturated amines compound is N1,N1-bis(2-(diethylamino)ethyl)-N2,N2-diethyl-diamine.

According to some embodiments of the present disclosure, there are no particular limits to a formulation of the medicament for resisting the radiation damage, provided that the saturated amines compound plays its role in repairing the radiation damage. According to an embodiment of the present disclosure, the medicament is formulated as an injection.

According to some embodiments of the present disclosure, there are no particular limits to a solvent of the injection, provided that such saturated amines compound is well dissolved in the solvent without an undesired effect. According to some embodiments of the present disclosure, the solvent of the injection is TE buffer with pH from 7.5 to 8.5, physiological saline, phosphate buffer solution (PBS), or a sterilized distilled water. Alternatively, the solvent of the injection is physiological saline.

According to some embodiments of the present disclosure, the medicament for resisting a radiation damage may be administrated with a dosage of 1.25 mg/kg to 10 mg/kg (body weight), alternatively 2.5 mg/kg (body weight), and the administration should be performed immediately after damaged by the radiation. In general, the medicament for resisting a radiation damage is injected every three days (i.e., being injected one day out of three), and 5 times within twelve days after damaged by the radiation. Both dosage and course of the treatment may be adjusted in accordance with practical conditions. Thereby, damaged cells and tissues may be repaired efficiently.

Further, the inventors further find out that the repairing effect of the saturated amines compound on the radiation damage may not be adversely influenced even if the saturated amines compound is modified into the form of sulfates or hydrochlorates. According to an embodiment of the present disclosure, the saturated amines compound is in the form of sulfate or hydrochlorate.

Further, one or more pharmaceutically acceptable carriers may be added into the medicament for resisting the radiation damage as required in practice. Specifically, according to some embodiments of the present disclosure, the carrier may be at least one of a diluent, an absorption enhancer and a surfactant conventionally-used in the pharmacy field.

In another aspect, the present disclosure provides in embodiments a method for treating or preventing a radiation damage. According to an embodiment of the present disclosure, the method includes a step of administrating a saturated amines compound to a desired subject, wherein the saturated amines compound is represented by the following formula I:

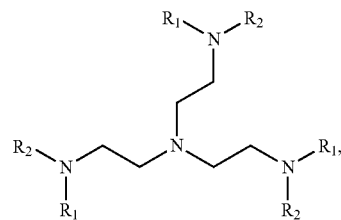

wherein each $R_1$ is independently H, $CH_3$ or $CH_2CH_3$; and each $R_2$ is independently H, $CH_3$ or $CH_2CH_3$.

The inventors find out that, damaged cells and tissues may be effectively repaired by administrating the medicament for resisting the radiation damage to a human or animal suffering a radiation damage. Specifically, the saturated amines compound may improve a recovery of a radiation-damaged hematopoietic system; in other words, the saturated amines compound may increase contents of WBC, RBC and PLT in peripheral blood, respectively; increase the number of all nucleated cells and the number of hematopoietic stem/progenitor cells in bone marrow (the number of CFU, and the number of CFU-G, CFU-GM and CFU-MK), and repair radiation-damaged intestinal, hepatic and pulmonary tissues.

According to an embodiment of the present disclosure, $R_1$ is $CH_3$, $R_2$ is $CH_3$, and the saturated amines compound is tris(2-(dimethylamino)ethyl)amine.

According to another embodiment of the present disclosure, $R_1$ is H, $R_2$ is H, and the saturated amines compound is N1,N1-bis(2-aminoethyl)ethane-1,2-diamine.

According to yet another embodiment of the present disclosure, $R_1$ is H, $R_2$ is $CH_3$, and the saturated amines compound is N1-methyl-N2,N2-bis(2-(methylamino)ethyl)ethane-1,2-diamine.

According to still yet another embodiment of the present disclosure, $R_1$ is H, $R_2$ is $CH_2CH_3$, and the saturated amines compound is N1-ethyl-N2,N2-bis(2-(ethylamino)ethyl)ethane-1,2-diamine.

According to still yet another embodiment of the present disclosure, $R_1$ is $CH_2CH_3$, $R_2$ is $CH_2CH_3$, and the saturated amines compound is N1,N1-bis(2-(diethylamino)ethyl)-N2,N2-diethyl-diamine.

According to some embodiments of the present disclosure, there are no particular limits to a formulation of the medicament for resisting the radiation damage, provided that the saturated amines compound plays its role in repairing the radiation damage. According to an embodiment of the present disclosure, the medicine is formulated as an injection.

According to some embodiments of the present disclosure, there are no particular limits to a solvent of the injection, provided that such saturated amines compound is well dissolved in the solvent without an undesired effect. According to some embodiments of the present disclosure, the solvent of the injection is TE buffer with pH from 7.5 to 8.5, physiological saline, phosphate buffer solution (PBS), or a sterilized distilled water. Alternatively, the solvent of the injection is physiological saline.

Further, the inventors further find out that the repairing effect of the saturated amines compound on the radiation damage may not be adversely influenced even if the saturated amines compound is modified into the form of sulfates or hydrochlorates. According to an embodiment of the present disclosure, the saturated amines compound is in the form of sulfate or hydrochlorate.

Further, one or more pharmaceutically acceptable carriers may be added into the medicament for resisting the radiation damage as required in practices. Specifically, according to some embodiments of the present disclosure, the carrier may be at least one of a diluent, an absorption enhancer and a surfactant conventionally-used in the pharmacy field.

It would be appreciated that the present disclosure is accomplished based on surprising discoveries by the inventor through a large amount of creative labors and optimizing work. In addition, it has been proved by experiments that, the saturated amines compound is capable of improving the recovery of the radiation-damaged hematopoietic system; in other words, the saturated amines compound is capable of increasing contents of WBC, RBC and PLT in peripheral blood, respectively; improving the proliferation of the hematopoietic stem/progenitor cells in bone marrow; and well-repairing intestinal, hepatic and pulmonary tissues of the irradiation-damaged mouse. The present disclosure provides a novel idea for researching and developing the medicament for resisting the radiation damage, has a wide application prospect and is of great significance.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Reference will be made in detail to embodiments of the present disclosure. The embodiments described herein with reference to drawings are explanatory, illustrative, and used to generally understand the present disclosure. The embodiments shall not be construed to limit the present disclosure.

Example 1

Synthesis of TA01

Figure 1:
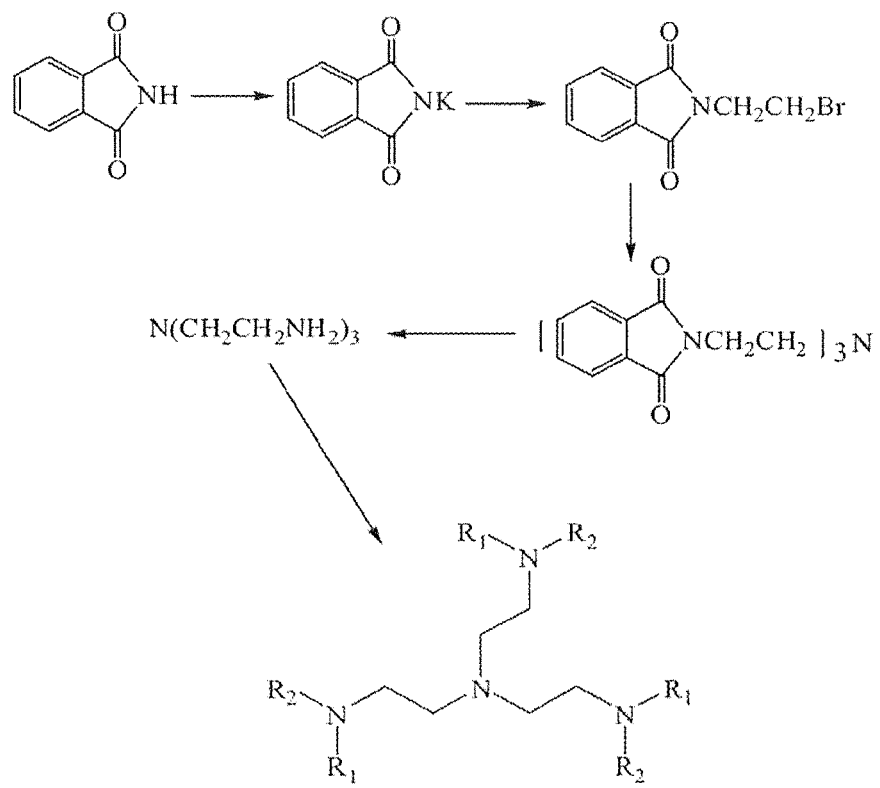
FIG. 1 is a schematic diagram showing a synthesis process of TA01.

Referring to FIG. 1, tris(2-(dimethylamino)ethyl)amine was synthesized with the following steps.

1) Synthesis of Phthalimide Potassium

A round-bottom flask containing 3200 mL dehydrated alcohol was added with 160.0 g phthalamide, and heated and refluxed for 0.5 h, until only a small amount of raw materials was not dissolved. The resulted hot solution was added into 61.0 g potassium hydroxide solution (including 60 mL water and 180 mL alcohol) by decantation, by which a white precipitate was formed immediately. Then the solution was cooled and filtered to obtain filtered residue, and alcohol was recycled. The filtered residue was washed with 400 mL acetone, 196.0 g phthalimide potassium was obtained, and the yield was 98.0%.

2) Synthesis of N-β-bromethyl phthalimide

A round-bottom flask equipped with a mixer and a refluxing-condensing tube was added with 150 g phthalimide potassium synthesized as above and 450 g 1,2-dibromoethane, heated at a temperature from 180° C. to 190° C. for 12 h by an oil bath. Excessive amounts of 1,2-dibromoethane was distilled out under a reduced pressure by the condensing tube, and about 290 g 1,2-dibromoethane was recovered. 30 mL alcohol was added into a mixture of N-β-bromethyl phthalimide and KBr prepared by the above process and refluxed for 0.5 h, until a black oil-like material was dissolved completely. The resulted hot solution was filtered immediately, and the KBr precipitate was washed with a small amount of hot alcohol, and then filtered solutions were combined and subjected to distillation under a reduced pressure to remove the alcohol, such that a dry residue was obtained.

The dry residue was added into 500 mL CS$_2$ solvent and refluxed for 15 min to 20 min, the resulted hot solution was filtered immediately, and CS$_2$ was distilled out under a reduced pressure, and then 131.0 g light brown crystal was obtained, i.e. N-β-bromethyl phthalimide. The yield was 63.6%. The melting point of the light brown crystal was 78° C. to 80° C.

3) Synthesis of β,β',β"-triphthalimidotriethylamine 46.0 g N-β-bromethyl phthalimide synthesized as above was heated to be melted, the temperature was maintained at 140° C. to 150° C., excessive amounts of dry NH$_3$ were supplied for reacting for 5 h to 8 h, and then 450 mL alcohol was added into the reaction mixture. The reaction system was heated and refluxed for 0.5 h and filtered, and the obtained precipitate was washed with hot alcohol and a small amount of water sequentially, and then recrystallized with glacial acetic acid. 25.2 g white crystal was then obtained, i.e. β,β',β"-triphthalimidotriethylamine. The yield was 78.0%, and the melting point of the white crystal was 187.5° C.

4) Synthesis of β,β',β"-triaminotriethylamine hydrochloride 50 mL concentrated HCl having a concentration of 120 mol/L was dropped into 20.0 g β,β',β"-triphthalimidotriethylamine synthesized as above, the temperature was maintained at about 150° C., and the reaction was maintained for 2 h. When the volume of the reaction system was reduced by about a half, the reaction system was filtered to filter out phthalic acid precipitate. The resulted filtrate was treated with hot alcohol having a volume 4 times of the filtrate, settled overnight, and 8.0 g white crystal was precipitated out, i.e. β,β',β"-triaminotriethylamine hydrochloride. The yield was 84.0%, and the melting point of the white crystal was 283° C.

5) Synthesis of β,β',β"-triaminotriethylamine 6.0 g β,β',β"-triaminotriethylamine hydrochloride synthesized as above and 2.6 g KOH (with a molar ratio of 1:2) were mixed uniformly, a small amount of $K_2CO_3$ was added to absorb water, amine was separated from the water phase, while a strong pungent smell was smelled, the vessel was sealed tightly. After filtering for overnight, two layers of filtrates were collected with a separatory funnel, respectively, and amine was present on the top of the light yellow solution. The solution was distilled under a reduced pressure to obtain a clear and transparent liquid, and such liquid was dried with metal Na and distilled under a reduced pressure, distilled under 135° C./9 mm Hg, and 1.6 g colorless condensed liquid was obtained, i.e. β,β',β"-triaminotriethylamine. The yield was 47.2%.

6) Synthesis of tris(2-(dimethylamino)ethyl)amine

The above obtained β,β',β"-triaminotriethylamine was subjected to a methylation reaction to obtain tris(2-(dimethylamino)ethyl)amine, i.e. saturated amines compound which is also referred to as TA01.

It would be appreciated that the above compound tris(2-(dimethylamino)ethyl)amine may be synthesized by methods disclosed in other documents. Similarly, other saturated amines compounds represented by formula I of the present disclosure, such as tris(2-(dimethylamino)ethyl)amine, N1,N1-bis(2-aminoethyl)ethane-1,2-diamine, N1-methyl-N2,N2-bis(2-(methylamino)ethyl)ethane-1,2-diamine, N1-ethyl-N2,N2-bis(2-(methylamino)ethyl)ethane-1,2-diamine, and N1,N1-bis(2-(diethylamino)ethyl)-N2,N2-diethyl-diamine, may be synthesized by methods in published documents.

Research shown in the following Examples 2-5 are made based on the tris(2-(dimethylamino)ethyl)amine (Code TA01) prepared in Example 1.

Example 2

The Survival Rate of Mice Radiated by $^{60}$Co γ Ray with a Lethal Dosage was Increased by Injecting TA01

50 male C57BL/6 mice were subjected to whole body irradiation by $^{60}$Co ray with a dosage rate of 1.56 Gy/min and an irradiation dosage of 8.0 Gy. The radiated mice were divided into 5 groups randomly, each group having 10 mice. The 5 groups were injected with TA01 with dosages of 0 mg/kg (control group), 1.25 mg/kg, 2.5 mg/kg, 5 mg/kg and 10 mg/kg, respectively. The injection was performed every three days and continued for 12 days, and the solvent of the injection was a PBS solution. Then, these mice were observed and survival rates of these mice were calculated.

Figure 2:
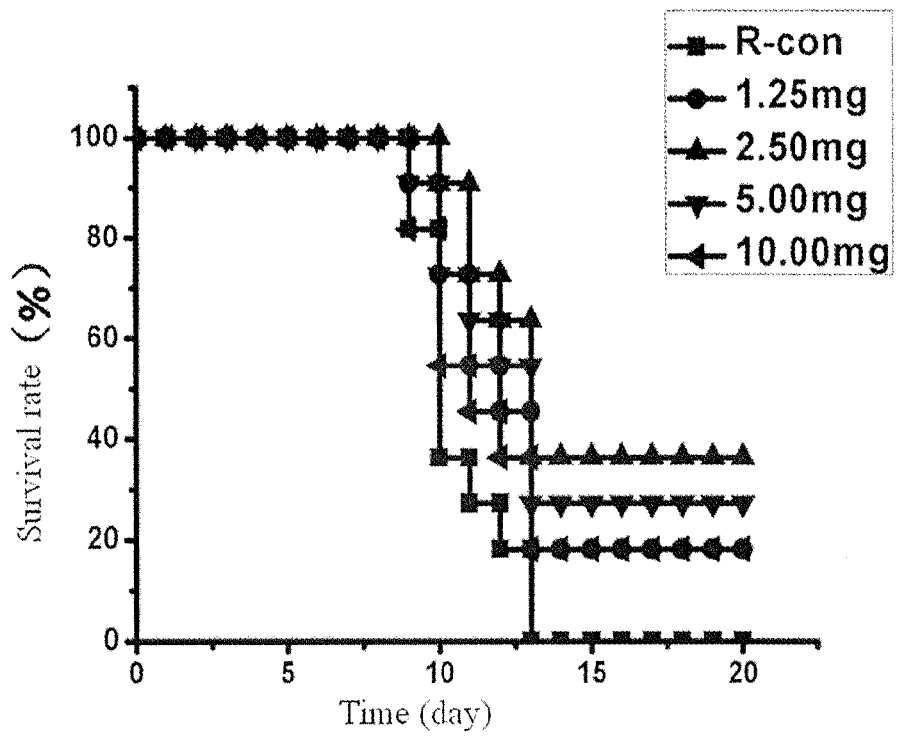
FIG. 2 is a diagram showing survival rates of mice radiated by $^{60}$Co γ-ray with a lethal dosage and subcutaneously injected with different dosages of TA01, according to an embodiment of the present disclosure.

FIG. 2 is a diagram showing survival rates (rates of survival) of mice radiated by $^{60}$Co γ-ray with a lethal dosage and subcutaneously injected with different dosages of TA01. As shown in FIG. 2, "R-con" represents an average survival rate of the control group, i.e. the group in which the mice were injected with 0 mg/kg TA01; and "TA01 1.25 mg/kg", "TA01 2.5 mg/kg", "TA01 5 mg/kg" and "TA01 10 mg/kg" represent survival rates of groups in which the mice were injected with corresponding doses of TA01, respectively. As can be seen from FIG. 2, the survival rates of mice radiated by $^{60}$Co γ-ray with a lethal dosage were significantly increased by injecting TA01 with doses of 1.25 mg/kg, 2.5 mg/kg, 5 mg/kg and 10 mg/kg every three days for 5 times, respectively, as compared with the control group. The mice injected with 2.5 mg/kg TA01 every three days were of the best survival rate.

Example 3

The contents of WBC, RBC and PLT in peripheral blood of mice radiated by $^{60}$Co γ-ray with a sub-lethal dosage were increased by injecting TA01.

10 male C57 mice were subjected to whole body irradiation by $^{60}$Co γ ray with a dosage rate of 1.56 Gy/min and an irradiation dosage of 6.5 Gy. The radiated mice were divided into 2 groups randomly, a PBS group having 5 mice and a TA01 group having 5 mice. Every mouse in the TA01 group was injected with 2.5 mg/kg (body weight) TA01 every three days for 5 times, and the solvent of the injection was a PBS solution. Every mouse in the PBS group was treated with the same process as the TA01 group, with the exception that the injection amount of TA01 was 0, in other words, only the PBS solution was injected. After different days for treating, each group of the mice was subjected to a cutting-tail process to collect 20 μL blood which was subsequently added with 2 mL blood cell dilution (commercially available from Jinan Bolai Biotechnology Co., Ltd). Then contents of WBC, PLT and RBC in blood were measured by a cell analyzer, and the results were shown in FIG. 3.

Figure 3:
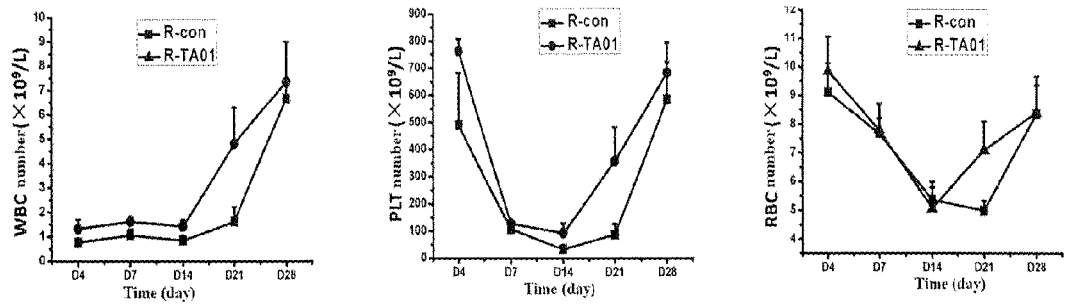
FIG. 3 is diagrams showing contents of WBC, RBC and PLT in peripheral blood of mice radiated by $^{60}$Co γ-ray with a sub-lethal dosage and subcutaneously injected with TA01 or PBS (control) at different time points, respectively, according to an embodiment of the present embodiment.

FIG. 3 is diagrams showing contents of WBC, RBC and PLT in peripheral blood of mice radiated by $^{60}$Co γ-ray with a sub-lethal dosage and injected subcutaneously with TA01 or PBS (control) at different time points. As shown in FIG. 3, * represents a significant difference of the TA01 group as compared with the PBS group. As can be seen from FIG. 3, the contents of WBC (significantly increased on the $4^{th}$, $7^{th}$ and $21^{st}$ day), PLT (significantly increased on the $4^{th}$, $14^{th}$, $21^{st}$, and $28^{th}$ day) and RBC (most obviously increased on the $21^{st}$ day) in periphery blood were increased by injecting the TA01, respectively, as compared with the PBS group.

Example 4

The number of hemopoietic stem/progenitor cells (the number of CFU; the number of CFU-G; CFU-GM and CFU-MK) in bone marrow of mice radiated by $^{60}$Co γ-ray with a sub-lethal dosage was increased.

Figure 4:
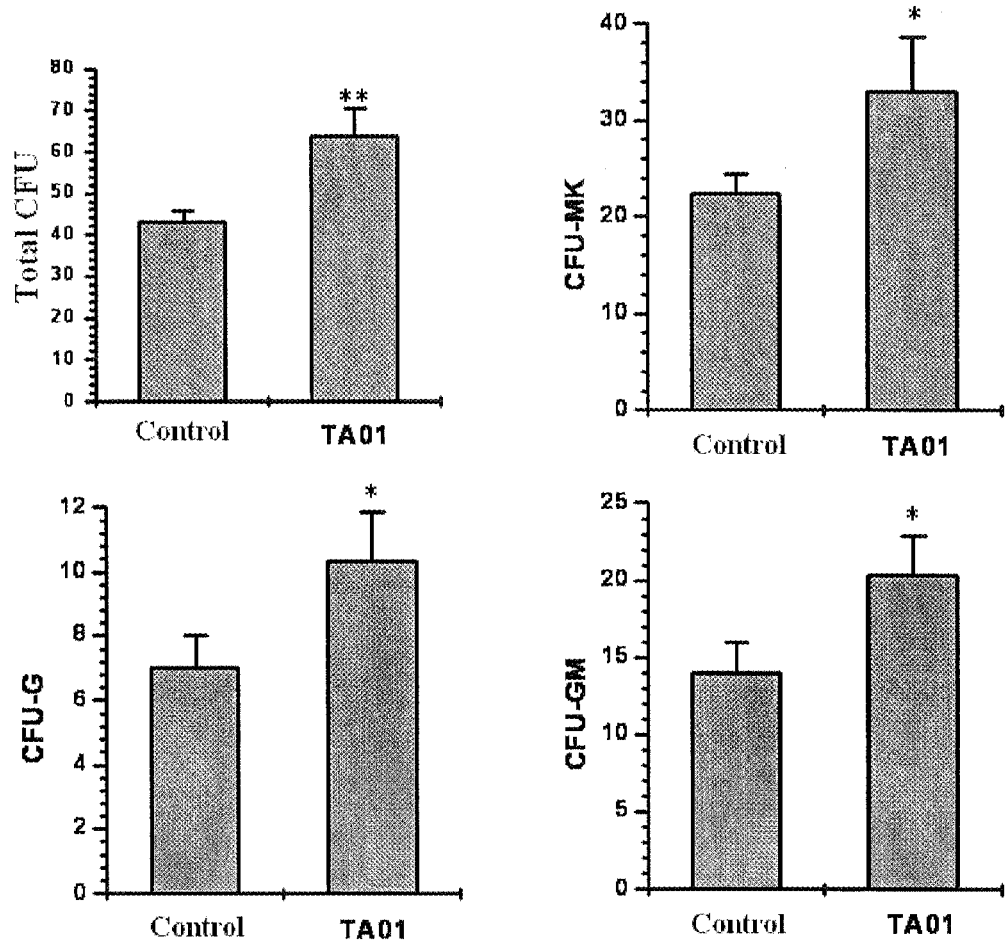
FIG. 4 is diagrams showing the numbers of hemopoietic progenitor cells (CFU, CFU-G, CFU-GM and CFU-MK) in bone marrow of mice radiated by $^{60}$Co γ-ray with a sub-lethal dosage and subcutaneously injected with TA01 or PBS (control), respectively, according to an embodiment of the present embodiment.

6 male C57/BL6 mice were subjected to whole body irradiation by $^{60}$Co γ ray with a dosage rate of 1.56 Gy/min and an irradiation dosage of 6.5 Gy. The radiated mice were divided into 2 groups randomly, a PBS group having 3 mice and a TA01 group having 3 mice. Every mouse in the TA01 group was injected with 2.5 mg/kg TA01 (body weight) every three days, the solvent of the injection was a PBS solution with pH from 7.5 to 8.5. TA01 injection dosage for the PBS group was 0, in other words, only the PBS solution was injected. On the $7^{th}$ day after the subcutaneous injection, bone marrow blood was collected from each mouse into respective 10 mL tubes pretreated with heparin (commercially available from Tianjing Haoyang Biological Product Technology Limited Liability Company). After the bone marrow blood was mixed with the heparin uniformly, fresh PBS (commercially available from Hyclone Company) was added therein up to 5 mL. After mixing, a uniform mixture of blood and PBS was obtained. Mouse lymphocyte separation medium (commercially available from Tianjing Haoyang Biological Product Technology Limited Liability Company) were subjected to pre-aliquot in centrifuge tubes each having 5 mL of the lymphocyte separation medium (operating in a super clean bench). Then the uniform mixture was gently added on the top of the lymphocyte separation medium, after which a centrifuge was performed at 1500 rpm/min for 20 min. The intermediate layer of cells in a white color was sucked into a new 10 mL centrifuge tube, which was then added with PBS up to 10 mL followed by a mixing and centrifuge at 1500 rpm/min for 5 min. Then obtained upper PBS was removed, and the tube was added with fresh PBS up to 10 ml followed by a mixing and centrifuge at 1500 rpm/min for 5 min. Then the upper PBS was removed, and the tube was added with fresh PBS up to 1 mL followed by a mixing, which was then subjected to a cell number counting. After calculating the number of single nucleus per mL blood, the blood was mixed uniformly with 500 μL semisolid medium (including 0.9% methylcellulose, 15% fetal bovine serum, 100 U/ml penicillin/streptomycin, 1 mM sodium pyruvate, 2 mM glutaminate, 2 mM PFHM II, 200 m/ml transferrin, 1% BSA, 0.45 mM MTG, 30% IMDM, 50 ng/ml SCF, 10 ng/ml TPO, 10 ng/ml IL-3, 10 ng/ml IL-11, 10 ng/ml GM-CSF and 3 U/ml EPO), and cultured in an incubator containing 5% $CO_2$ at 37° C. After 7 days, hematopoietic colony-forming unit (CFU), granulocyte colony-forming unit (CFU-G), granulocyte and macrophage colony-forming unit (CFU-GM) and megakaryocyte colony-forming unit (CFU-MK) were counted respectively, and the results were shown in FIG. 4. FIG. 4 is diagrams showing the numbers of hemopoietic stem/progenitor cells (CFU, CFU-Q CFU-GM, and CFU-MK) in bone marrow of mice radiated by $^{60}$Co γ-ray with and subcutaneously injected with TA01 or PBS (control). As shown in FIG. 4, the number of total colony-forming units (CFU) of mice in the TA01 group was increased significantly as compared with the control group, in which the numbers of CFU-G, CFU-GM and CFU-MK were all increased obviously. This indicates that TA01 can increase the number of hemopoietic stein/progenitor cells in bone marrow of the radiation-damaged mice, i.e. increase the numbers of CFU-G; CFU-GM and CFU-MK in bone marrow of the radiation-damaged.

Example 5

Injecting TA01 can Improve Repair of Intestine Tissue, Liver Tissue and Lung Tissue of a Mouse Subjected to Lethal Doses of Radiations 6 male C57/BL6 mice were subjected to whole body irradiation by $^{60}$Co γ ray with a dosage rate of 1.56 Gy/min and an irradiation dosage of 8.0 Gy. The radiated mice were divided into 2 groups randomly, a PBS group (control) having 3 mice and a TA01 group having 3 mice. Every mouse in the TA01 group was injected with 2.5 mg/kg TA01 (body weight) every three days, the solvent of the injection was a PBS solution with pH of 7.4. TA01 injection dosage for the PBS group was 0, in other words, only the PBS solution was injected. The mice both two groups were sacrificed by dislocation on the $10^{th}$ day and the $14^{th}$ day after the irradiation, respectively. The intestinal, hepatic and pulmonary tissues were collected, fixed with 4% paraformaldehyde and formed into paraffin sections. The paraffin sections were subjected to HE staining, so as to obserse repairing conditions of the intestinal, hepatic and pulmonary tissues, and the results were shown in FIGS. 5 and 6.

Figure 5:
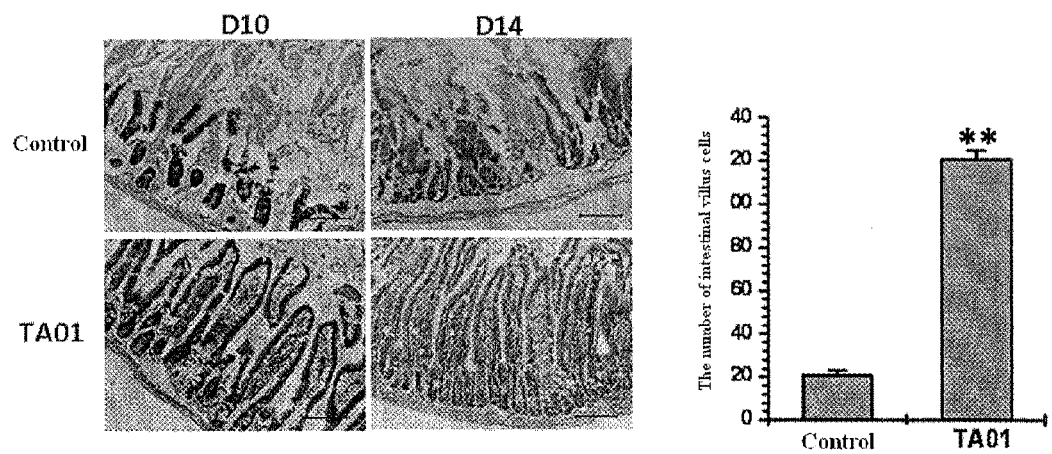
FIG. 5 is diagrams showing results of hematoxylin-eosin staining with intestinal tissues of mice radiated by $^{60}$Co γ-ray with a lethal dosage and treated with TA01 or PBS, according to an embodiment of the present embodiment.

FIG. 5 is diagrams showing results of hematoxylin-eosin staining with intestinal tissues of mice radiated by $^{60}$Co γ-ray with a lethal dosage and treated with TA01 or PBS. As shown in FIG. 5, the left diagram shows the HE staining results of the intestinal tissue of mice in the PBS group and the TA01 group, respectively, on the $10^{th}$ and $14^{th}$ day after the injection; and the right diagram shows results of the numbers of intestinal villus cells of mice in the PBS group and the TA01 group, respectively.

Figure 6:
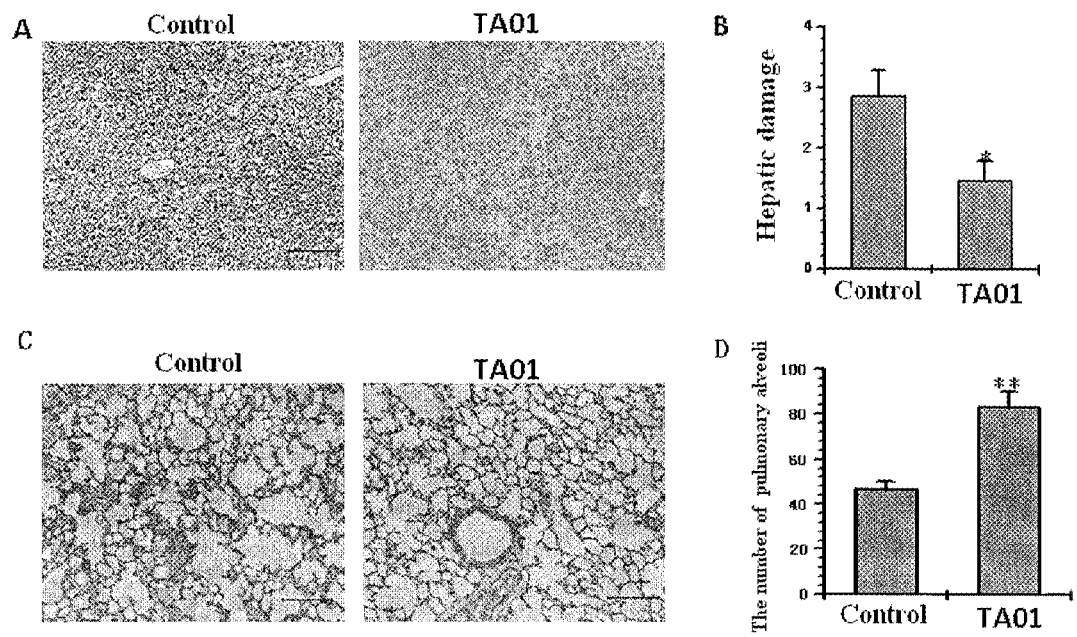
FIG. 6 is diagrams showing results of hematoxylin-eosin staining with hepatic and pulmonary tissue of mice radiated by $^{60}$Co γ-ray with a lethal dosage and treated with TA01 or PBS, according to an embodiment of the present embodiment.

FIG. 6 is diagrams showing results of hematoxylin-eosin staining with hepatic and pulmonary tissue of mice radiated by $^{60}$Co γ-ray with a lethal dosage and treated with TA01 or PBS. As shown in FIG. 6, FIG. 6A shows HE staining results of hepatic tissue of mice in the PBS group and the TA01 group, respectively; FIG. 6B shows a comparison of a hepatic damage between mice in the PBS group and the TA01 group; FIG. 6C shows HE staining results of pulmonary tissue of mice in the PBS group and the TA01 group, respectively; and FIG. 6D shows a comparison of the numbers of pulmonary alveoli per unit area of mice in the PBS group and the TA01 group. As can be seen from FIGS. 5 and 6, injecting TA01 can improve repairs of intestinal, hepatic and pulmonary tissues of mice radiated by $^{60}$Co γ-ray with a lethal dosage.

Referring to the above Examples 2-5 which were illustrated by taking tris(2-(dimethylamino)ethyl)amine as an example, it proves the saturated amines compound represented by the formula I is capable of efficiently improving repair of the radiation-damaged hematopoietic system, i.e. increasing the contents of WBC, RBC and PLT in the peripheral blood of an radiation-damaged animal, respectively; improving proliferations of thehematopoietic stem/progenitor cells in the bone marrow; and well-repairing the intestinal, hepatic and pulmonary tissues of the irradiation-damaged mouse. It should be appreciated that the present disclosure further proves that other saturated amines compounds represented by the formula I, such as N1,N1-bis(2-aminoethyl)ethane-1,2-diamine, N1-methyl-N2,N2-bis(2-(methylamino)ethyl)ethane-1,2-diamine, N1-ethyl-N2,N2-bis(2-(ethylamino)ethyl)ethane-1,2-diamine, and N1,N1-bis(2-(diethylamino)ethyl)-N2,N2-diethyl-diamine, also have the above effects, thus proves that saturated amines compounds may be used to efficiently prepare the medicament for resisting the radiation damage.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for treating or preventing a radiation damage, comprising a step of administrating a saturated amines compound to a desired subject, wherein the saturated amines compound is represented by the following formula I:

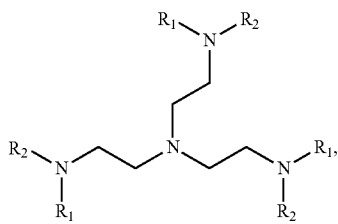

wherein each $R_1$ is independently H, $CH_3$ or $CH_2CH_3$; and each $R_2$ is independently H, $CH_3$ or $CH_2CH_3$.

2. The method of claim 1, wherein $R_1$ is $CH_3$, $R_2$ is $CH_3$, and the saturated amines compound is tris(2-(dimethylamino)ethyl)amine.

3. The method of claim 1, wherein $R_1$ is H, $R_2$ is H, and the saturated amines compound is N1,N1-bis(2-aminoethyl)ethane-1,2-diamine.

4. The method of claim 1, wherein $R_1$ is H, $R_2$ is $CH_3$, and the saturated amines compound is N1-methyl-N2,N2-bis(2-(methylamino)ethyl)ethane-1,2-diamine.

5. The method of claim 1, wherein $R_1$ is H, $R_2$ is $CH_2CH_3$, and the saturated amines compound is N1-ethyl-N2,N2-bis(2-(ethylamino)ethyl)ethane-1,2-diamine.

6. The method of claim 1, wherein $R_1$ is $CH_2CH_3$, $R_2$ is $CH_2CH_3$, and the saturated amines compound is N1,N1-bis(2-(diethylamino)ethyl)-N2,N2-diethyl-diamine.

7. The method of claim 1, further comprising a step of forming the saturated amines compound in a form of an injection.

8. The method of claim 7, wherein a solvent of the injection is TE buffer with pH from 7.5 to 8.5, physiological saline, phosphate buffer saline (PBS) or a sterilized distilled water.

9. The method of claim 1, wherein the saturated amines compound is in a form of sulfate or hydrochlorate.

* * * * *